(12) United States Patent
Wöhrle (10) Patent No.: US 6,174,167 B1
(45) Date of Patent: Jan. 16, 2001

(54) BIOROOT ENDOSSEOUS IMPLANT

(76) Inventor: Peter S. Wöhrle, 7 Carmel Bay Dr., Corona del Mar, CA (US) 92625

( * ) Notice: Under 35 U.S.C. 154(b), the term of this patent shall be extended for 0 days.

(21) Appl. No.: 09/203,822

(22) Filed: Dec. 1, 1998

(51) Int. Cl.$^7$ .................................................. A61C 8/00

(52) U.S. Cl. ........................................... 433/173; 433/174

(58) Field of Search .................................. 433/173, 172, 433/174, 223

(56) References Cited

U.S. PATENT DOCUMENTS

| | | | |
|---|---|---|---|
| 2,112,007 | 3/1938 | Adams | 433/174 |
| 4,416,629 | 11/1983 | Mozsary et al. | 433/173 |
| 4,624,673 | 11/1986 | Meyer | 623/16 |
| 4,960,381 | 10/1990 | Niznick | 433/174 |
| 5,246,370 | * 9/1993 | Coatoam | 433/173 |
| 5,282,746 | * 2/1994 | Sellers et al. | 433/172 |
| 5,417,568 | * 5/1995 | Giglio | 433/173 |
| 5,417,569 | * 5/1995 | Perisse | 433/173 |
| 5,584,693 | * 12/1996 | Nishihara | 433/169 |
| 5,636,989 | * 6/1997 | Somborac et al. | 433/173 |

FOREIGN PATENT DOCUMENTS

| | | |
|---|---|---|
| 413224 | 5/1966 | (CH) . |
| 1291470 | 10/1972 | (GB) . |
| 540713 | 3/1956 | (IT) . |

OTHER PUBLICATIONS

Baier, et al., 1988, "Future Directions in Surface Preparation of Dental Implants", *Journal of Dental Education*, 52:788–791.

Bengazi, et al., 1996, "Recession of the soft tissue margin at oral implants", *Clinical Oral Implants Research*, 7:303–310.

Brånemark, et al., 1985, "Tissue–Integrated Prostheses", *Quintessence Publishing Co., Inc.*, p. 11–76.

John B. Brunski, 1988, "Biomechanics of Oral Implants: Future Research Directions", *Journal of Dental Education*, 52:775–787.

Buser, et al., 1991, "Tissue Integration of One–Stage ITI Implants: 3–Year Results of a Longitudinal Study With Hollow–Cylinder and Hollow–Screw Implants", *The International Journal of Oral & Maxillofacial Implants*, 6:405–412.

Buser, et al., 1996, "Comparison of healed tissues adjacent to submerged and non–submerged unloaded titanium dental implants", *Clinical Oral Implants Research*, 7:11–19.

Chiche, et al., 1998, "Multidispilinary Implant Dentistry for Improved Aesthetics and Function", *Pract Periodont. Aesthet. Dent.*, 10:177–186.

Gomez–Roman, et al., 1997, "The Frialit–2 Implant System: Five–Year Clinical Experience in Sungle–Tooth and Immediately Postextraction Applications", *The International Journal of Oral & Maxillofacial Implants*, 12:299–309.

"Implantatsysteme und ihre Komponenten", 1998, *Implantologie*; 1:75–79.

Jansen, et al., 1997, "Microbial Leakage and Marginal Fit of the Implant–Abutment Interface", *The International Journal of Oral & Maxillofacial Implants*, 12:527–540.

Kirsch, et al., 1989, "The IMZ Osteointegated Implant System", *Dental Clinics of North America*, 33:733–791.

(List continued on next page.)

Primary Examiner—John J. Wilson
Assistant Examiner—Melba Bumgarner
(74) Attorney, Agent, or Firm—Pennie & Edmonds LLP (57) ABSTRACT

Novel endosseous implants, are designed so that the areas intended for bone and soft tissue apposition exhibit a scalloped appearance, including both convex and concave patterns, to follow the naturally occurring bone and soft tissue morphology. Thus, the implants provide attachment possibilities for both bone and soft tissue, thereby effecting both hard- and soft-tissue preservation.

26 Claims, 5 Drawing Sheets

OTHER PUBLICATIONS

Jack T. Krauser, DMD, Oct. 1989, "Hydroxylapatite–Coated Dental Implants", *Dental Clinics of North America,* 33:879–903.

Langer, et al., 1993, "The Wide Fixture: A Solution for Special Bone Situations and a Rescue for the Compromised Implant. Part 1", *The International Journal of Oral & Maxillofacial Implants,* 8:400–408.

Roland M. Meffert, DDS, 1988, "The Soft Tissue Interface in Dental Implantology", *Journal of Dental Education,* 52:810–811.

Olsson, et al., 1995, "Mkll–A Modified Self–Tapping Brånemark Implant: 3–Year Results of a Controlled Prospective Pilot Study", *The International Journal of Oral & Maxillofacial Implants,* 10:15–21.

Prestipino, et al., Jan./Feb. 1993, "Esthetic High–Strength Implant Abutments. Part 1", *Journal of Esthetic Dentistry,* p. 29–35.

W. Eugene Roberts, DDS, Ph.D., 1998, "Bone Tissue Interface", *Journal of Dental Education,* 52:804–809.

Saadoun, et al., 1998, "Periodontal Implications in Implant Treatment Planning for Aesthetic Results", *Pract. Periodont. Asthet. Dent.,* 10: 655–664.

Schnitman, et al., 1988, "Implants for Partial Edentulism", *Journal of Dental Education,* 52:725–736.

Siegele, et al., 1989, "Numerical Investigations of the Influence of Implant Shape on Stress Distribution in the Jaw Bone", *The International Journal of Oral & Maxillofacial Implants,* 4:333–340.

Sullivan, et al., May/Jun. 1993, "Considerations for Successful Single Tooth Implant Restorations", *Journal of Esthetic Dentistry,* 5:119–124.

Wennerberg, et al., 1993, "Design and Surface Characteristics of 13 Commercially Available Oral Implant Systems", *The International Journal of Oral & Maxillofacial Implants,* 8:622–633.

F.A. Young, D.Sc., 1988, "Future Directions in Dental Implants Materials Research", *Journal of Dental Education,* 52:770–774.

\* cited by examiner

BIOROOT ENDOSSEOUS IMPLANT

FIELD OF INVENTION

The present invention relates generally to the field of implant dentistry, and more particularly to the design of one- and two-stage endosseous implants.

BACKGROUND OF THE INVENTION

Endosseous, i.e., intra boney, implants are commonly used to support fixed or removable prostheses where a patient's natural roots have been lost, and as a consequence, support is lacking to provide an adequate foundation onto which the dentist can rebuild a dentition. As the aging population retains more of their natural teeth, and as the younger generations want to take advantage of more conservative approaches offered by implant dentistry, e.g., using a single implant rather than cutting down adjacent teeth to support a short span bridge to replace a missing tooth, implant dentistry has gained more and more popularity and has moved into the mainstream of dentists worldwide.

The current implant design is based on an endosseous fixture, a titanium screw that acts as an artificial root. Br ånemark, *Tissue-Integrated Prostheses* (1985). Modifications made to the endosseous fixture have centered on the macro structure of the implant (e.g., by exchanging the screw with a press-fit/cylindrical implant, a stepped screw or cylinder, or a tapered screw or cylinder), (Brunski J. B., *Biomechanics Of Oral Implant,. Future Research Directions* NIH Consensus Development Conference on Dental Implants, 1988; Kirsch A. et al., *The IMZ Osseointegrated Implant System*, Dent. Clin. North Am. 1989 (4), 33:733–791; Niznick G. A., A *Multimodal Approach To Implant Prosthodontics*, Dent. Clin. North Am. 1989 (4), 33:869–878; Wennerberg A. et al., *Design And Surface Characteristics Of* 13 *Commercially Available Oral Implant Systems, Id.* 1993:8:622–633; Siegele D. et al., *Numerical Investigations Of The Influence Of Implant Shape On Stress Distribution In The Jaw Bone, Id.*, 1989:4:333–340; Olsson M. et al., *MkII-a Modified Self-Tapping Brånemark Implant: 3-Year Results, Id.* at 1995:10:15–21; Langer B. et al., *The Wide Fixture: A Solution For Special Bone Situations And A Rescue For The Compromised Implant, Part* 1*, Id.*, 1993:8:400–408; Schnitman P. A. et al., *Implants For Partial Edentulism, NIH* Consensus Development Conference On Dental Implants, 1988), on the micro structure (e.g., surface modifications such as use of machined titanium, blasted titanium, titanium alloy, acid-etched titanium, plasma-sprayed titanium and hydroxyappatite coating, growth factors, and proteins), (Baier R. E. et al., *Future Directions In Surface Preparation Of Dental Implants*, NIH Consensus Development Conference On Dental Implants, 1988; Young F. A., *Future Directions In Dental Implant Materials Research, Id.*; Krauser J., *Hydroxylappatite-Coated Dental Implants*, Dent. Clin. North Am. 1989, 33:4:879–903; Buser D. et al., *Tissue Integration Of One-Stage ITI Implants*: 3-*Year Results Of A Longitudinal Study With Hollow-Cylinder And Hollow-Screw Implants*, Int. J. Oral Maxillofac. Implants, 1991:6:405–412), on one-vs-two-stage designs, (Weber H. P. et al., *Comparison Of Healed Tissues Adjacent To Submerged And Non-Submerged Unloaded Titanium Dental Implants*, Clin. Oral Impl. Res. 1996:7:11–19; Busser D. et al., *Tissue Integration Of One-Stage ITI Implants*: 3-*Year Results Of A Longitudinal Study With Hollow-Cylinder and Hollow-Screw Implants*, Int. J. Oral Maxillofac Implants 1991:6:405–412), and on modifying the connection between the implant and its abutment (e.g, either internal hex, external hex, standard hex, tall hex, wide hex, etc.), (U.S. Pat. No. 4,960,381; U.S. Pat. No. 5,407,359; U.S. Pat. No. 5,209,666; U.S. Pat. No. 5,110, 292).

Irrespective of the design variables discussed above, current systems have two general characteristics in common: First, the abutment-implant interface is planar; and second, the area intended for bone apposition, i.e., osseointegration, terminates parallel to the abutment-implant interface, 360 degrees around the implant.

Traditionally, endosseous implants were designed for treatment of the fully edentulous patient. In general, this particular patient population exhibits reduced bone-tissue volume, both in height and width when compared to the partially edentulous patient with recent or impending tooth loss. However, the bone-tissue morphology of partially edentulous patients significantly differs from that of fully edentulous patients, in that the naturally occurring supporting bone structures reveal a scalloped architecture around the tooth.

Currently available implant technology does not take the different bone-tissue morphologies into consideration. Heretofore use of an implant with an intended bone-tissue apposition surface parallel to a flat abutment-implant interface has led to either (1) placement of soft-tissue intended parts of the implant within bone-tissue, leading to bone-tissue resorption in these areas, and/or (2) exposure of hard-tissue intended surfaces to the soft tissue, resulting in possible peri-implant infections due to bacterial colonization around the rough surface and potential loss of the implant.

SUMMARY OF THE INVENTION

Novel endosseous implants, which are structured to better maintain hard and soft-tissue in the area where the implant exits from the bone-tissue and transverses the soft-tissue. More particularly, the implants of the present invention are designed so that areas intended for hard- and soft-tissue apposition exhibit a scalloped appearance, including convex and/or concave patterns, disclosed approximate the naturally occurring bone morphology. Thus, the implants of the present invention provide substantially increased attachment possibilities for both bone-tissue and soft-tissue, thereby facilitating bone-tissue and soft-tissue preservation and maintenance.

The present invention will enable the surgeon to place an implant into residual bone with the surface of the implant intended for bone-tissue contact and apposition (machined or roughened, surface coated or textured, altered with biologic modifiers such as proteins and growth factors, or any combination thereof) being substantially in contact with bone-tissue, and with the surface intended for soft-tissue apposition (polished/treated with soft tissue specific surface modifications) being substantially in contact with soft-tissue.

More specifically, the implant, according to an embodiment of the present invention, is a substantially cylindrical shaft made from a biocompatible material having a distal end and a proximal end. A bone-tissue/soft-tissue transition region and a abutment-implant interface are both disposed towards the proximal end of the shaft. The bone-tissue/soft-tissue transition region is defined as the approximate region of the shaft and/or the abutment-implant interface where the implant exits the bone-tissue and transverses into the soft-tissue. The bone-tissue/soft-tissue transition region has a bone-tissue apposition surface configured to approximate the physiological contours of the alveolar bone. In a two-stage implant, the abutment-implant interface may be either substantially planar, approximately 90° to the longitudinal axis of the shaft, or contoured to approximate the contour of the alveolar bone. In a one-stage implant the abutment is permanently attached to the abutment-implant interface, or an integral part of the implant itself. The abutment, in both one-and two-stage implants, has an abutment-crown interface, which is either substantially planar or contoured to approximate the contour of the alveolar bone, and a chimney onto which the crown is secured.

An implant constructed according to the principles of the present invention facilitates hard- and soft-tissue maintenance, increases longevity of the implant and improves its aesthetic appearance. As will be readily apparent to the skilled artisan, the present invention may be applied to numerous prosthetic applications, such as, but not limited to, a single tooth replacement, an abutment for a bridge (fixed partial denture) regardless of the nature of the other abutment (natural tooth or implant), a pier abutment or an over denture abutment.

DETAILED DESCRIPTION OF THE PREFERRED EMBODIMENTS

Figure 1:
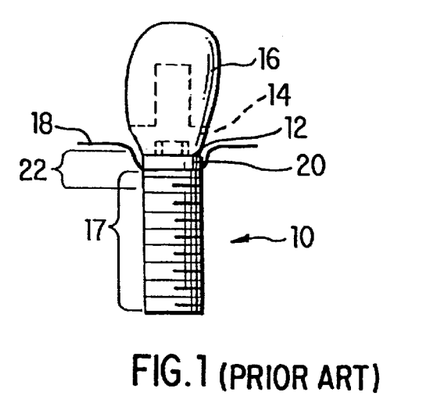
FIG. 1 depicts a frontal view of a prior art implant.
Figure 2:
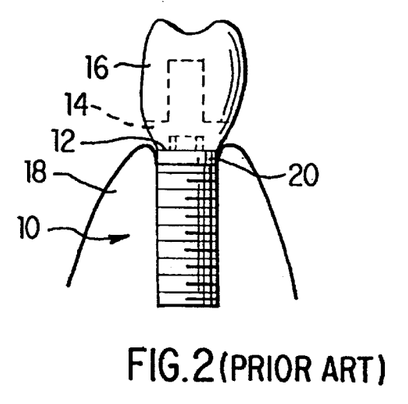
FIG. 2 depicts an interproximal view of the prior art implant in FIG. 1.

FIGS. 1 and 2 show prior art implant 10, abutment-implant interface 12, abutment 14 and crown 16 constructed according to the current state of the art. Implant 10, according to the current state of the art, has a bone apposition surface 17, typically threads or otherwise roughened surface, extending into alveolar bone 18. Abutment-implant interface 12 extends partially into the alveolar bone and has polished surface 20, which is not suitable for bone apposition. Use of implant 10, constructed according to the current state of the art, results in bone-tissue resorption in bone-tissue/soft-tissue transition region 22 because polished surface 20 contacts bone-tissue, which as discussed, leads to bone resorption. Any loss of natural bone structure or topography is highly undesirable from both structural and aesthetic perspectives. Even the smallest bone-tissue loss between the tooth and an implant will lead to soft-tissue shrinkage due to lack of boney support, resulting in "black triangles" (open spaces) between the teeth-a highly unaesthetic situation.

Figure 3:
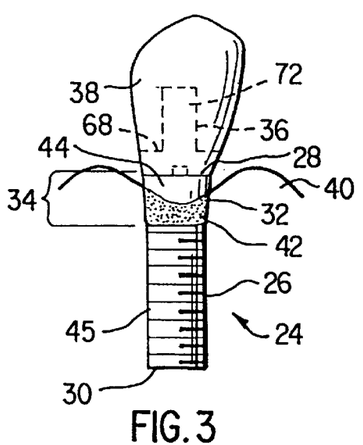
FIG. 3 depicts a frontal view an implant according to an embodiment of the present invention.
Figure 4:
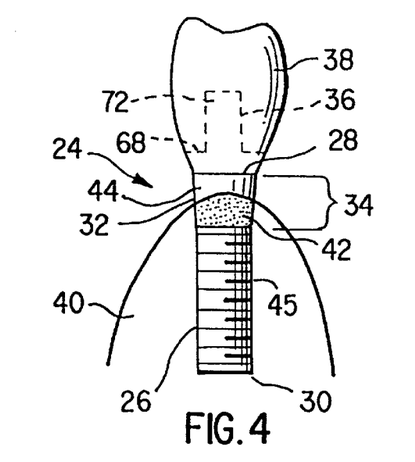
FIG. 4 depicts an interproximal view of the implant in FIG. 3.

FIGS. 3 and 4 show a two-stage implant according to an embodiment of the present invention. Implant 24 has shaft 26, substantially planar abutment-implant interface 28, distal end 30, proximal end 32 and bone-tissue/soft-tissue transition region 34. Abutment 36 and crown 38 are attached to implant 24 using means well known to the skilled artisan for two-stage implants. Implant 24 is made from a biocompatible material, including but not limited to, metal, ceramic, glasses or any combination thereof. Preferably implant 24 is made from titanium or an alloy thereof.

Bone-tissue/soft-tissue transition region 34 has a scalloped bone-tissue apposition surface 42, which approximately follows the naturally occurring contours of existing bone 40, and a scalloped soft-tissue apposition surface 44, which approximately follows the naturally occurring contours of the existing soft-tissue (not shown). Thus, there are two distinctive scalloped tissue-attachment surfaces: bone-tissue apposition surface 42 to maintain the naturally occurring bone-tissue morphology; and soft-tissue apposition surface 44 to maintain the naturally occurring soft-tissue morphology. The degree of scalloping or the height of the convex and concave regions depends on, inter alia, the degree of existing bone-tissue resorption, the size of the implant, the implant location within the arch, the bone morphology and the soft-tissue morphology. The dimensions are similar to the scalloped appearance of the cemento-enamel (CE) junction observed on natural teeth. The vertical difference between the highest and lowest point of the scalloped margin ranges from less than 1 mm on posterior teeth to approximately 3–5 mm on anterior teeth. By way of example, bone-tissue apposition surface 42 can be obtained by machining, application of textured surfaces, acid etching, blasting with particles, applying growth factor, applying protein, or other materials that promote, enhance, and/or maintain bone-tissue growth and/or apposition. Also by way of example, soft-tissue apposition surface 44 can be achieved by polishing or other treatment that leaves a surface to promote, enhance, and/or maintain soft-tissue growth and/or apposition. Below the bone-tissue/soft-tissue transition region 34, shaft 26 has threads 45, or other means well known in the art, to anchor the implant into the alveolar bone.

In use, the surgeon inserts distal end 30 into the alveolar bone such that bone-tissue apposition surface 42 and soft-tissue apposition surface 44 approximately mirror the existing bone- and soft-tissue morphology respectively. The implant should be aligned such that the highest points of bone apposition surface 42 are substantially aligned with the interproximal areas of the bone-tissue and such that the lowest points are substantially aligned with the buccal and lingual area of the bone-tissue. In a two-stage process, the surgeon sutures tissue over the implant, waits several months for the bone to adhere to the implant, opens the tissue, attaches abutment 36 to abutment-implant interface 28 and attaches crown 38 to abutment 36. Bone-tissue apposition surface 42 and soft-tissue apposition surface 44 maintain bone- and soft-tissue attachment levels and facilitate prevention of peri-implant infections, which occur due to increased peri-implant pocket depths frequently observed with the prior art implant designs. Therefore, implants constructed according to the present invention increase the longevity of the implant and improve the aesthetic appearance of the restoration.

Figure 5A:
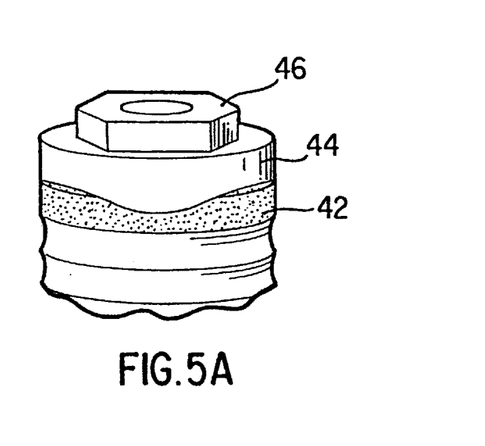
FIG. 5A depicts a three-dimensional top frontal view of the implant in FIG. 3.
Figure 5B:
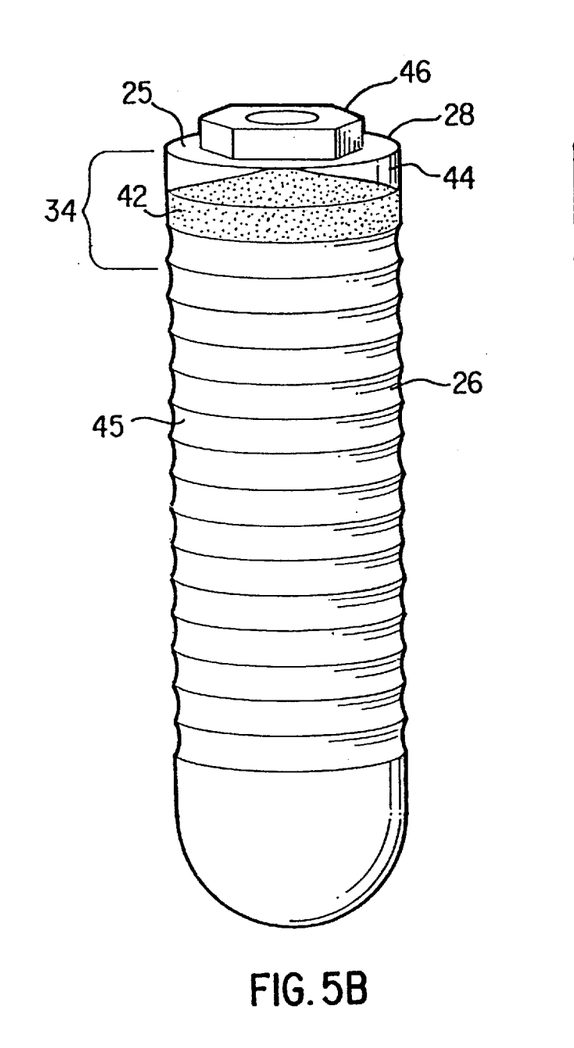
FIG. 5B depicts a three-dimensional interproximal top view of the implant in FIG. 3
Figure 6:
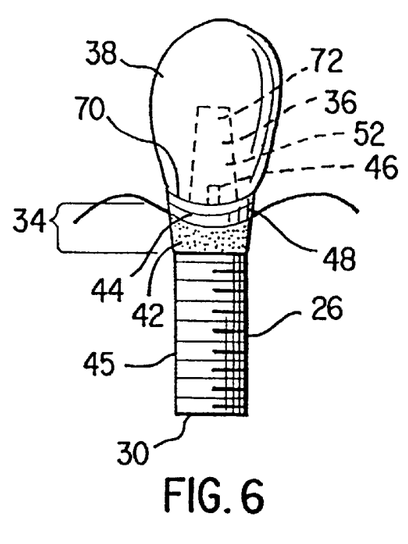
FIG. 6 depicts a frontal view of an implant according to another embodiment of the present invention.
Figure 7:
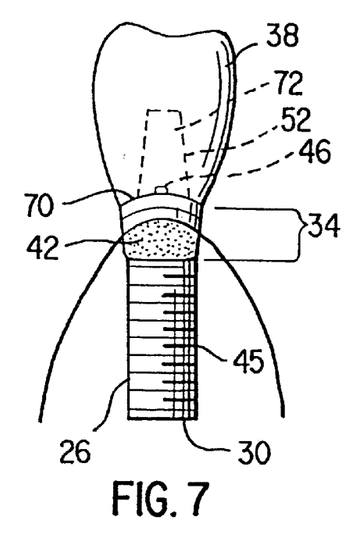
FIG. 7 depicts an interproximal view of the implant in FIG. 6.
Figure 8:
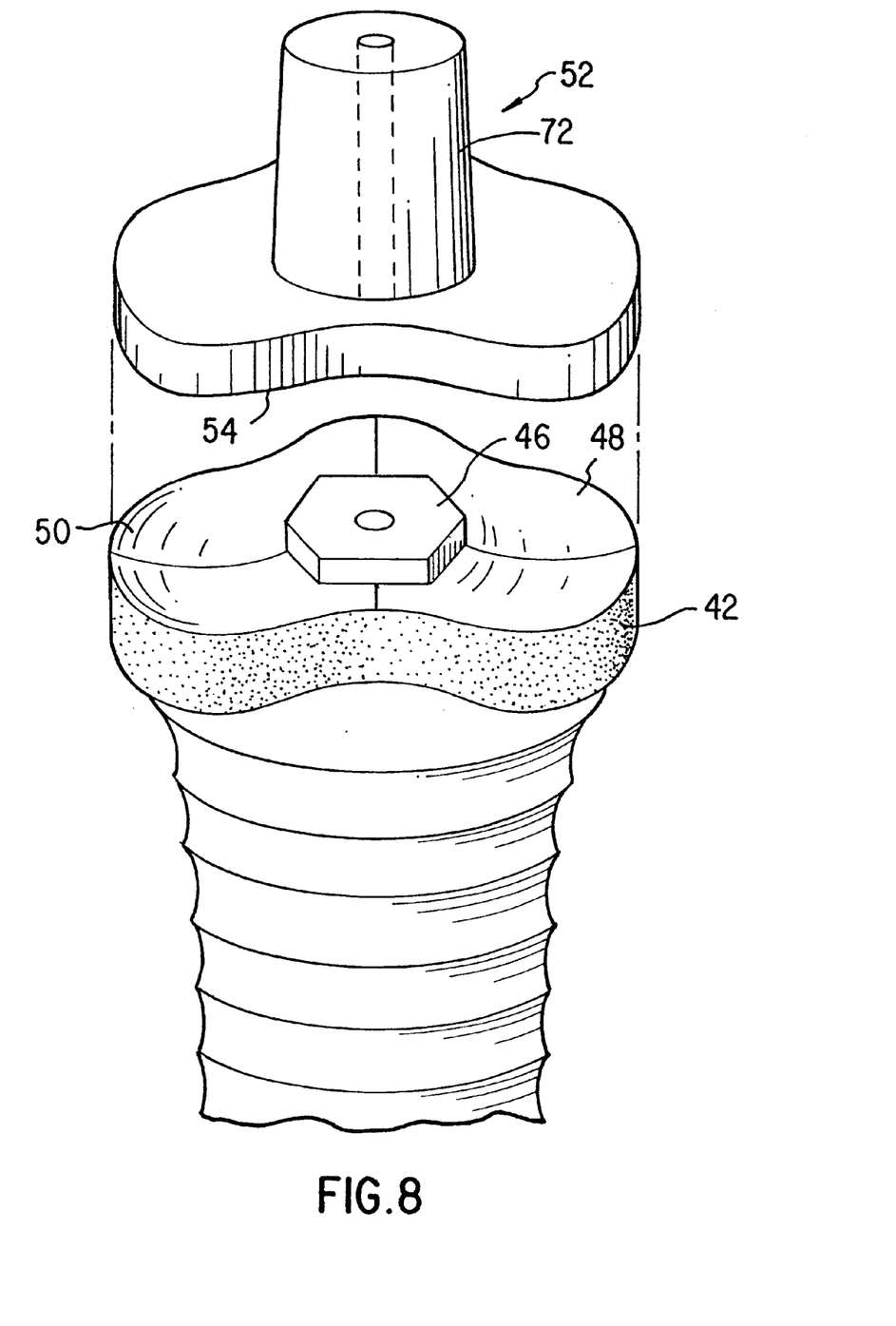
FIG. 8 depicts a three-dimensional top view of the implant in FIG. 6.

Referring to FIGS. 5A and 5B, abutment-implant interface 28 has substantially planar upper surface 25, which is approximately 90° to the longitudinal axis of shaft 26, and connecting means 46 for connecting abutment 36 (FIGS. 3 and 4) to abutment-implant interface 28. Connecting means 46 is well known in the art and includes, but is not limited to, internal hex, external hex, standard hex, tall hex, wide hex or camlog. In an alternative embodiment of the present invention, as shown in FIGS. 6–8, abutment-implant interface 48 has at least its edges contoured to approximate the contours of the alveolar bone, thereby defining a contoured upper surface 50 (FIG. 8) surrounding connecting means 46. Also provided in this alternative embodiment is abutment 52, which has lower contoured surface 54 configured to substantially mate with contoured upper surface 50. The upper and lower contoured surfaces provide additional lateral support between abutment 52 and abutment-implant interface 48. Additionally, contoured upper surface 48 of this alternative embodiment results in a narrower depth between gum line 54 and abutment-implant interface 48 (FIGS. 6 and 7), thus enhancing longevity of the restoration as a result of decreased pocket depths.

Figure 9:
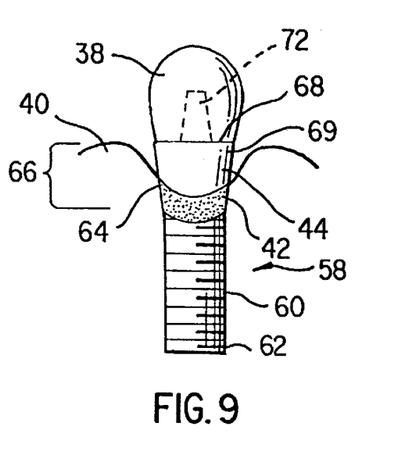
FIG. 9 shows a frontal view of an implant according to another embodiment of the present invention.
Figure 10:
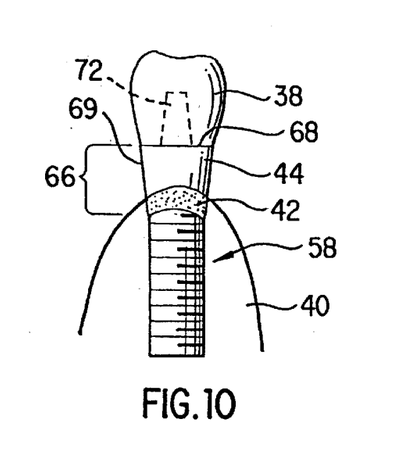
FIG. 10 depicts an interproximal view of the implant in FIG. 9.
Figure 11:
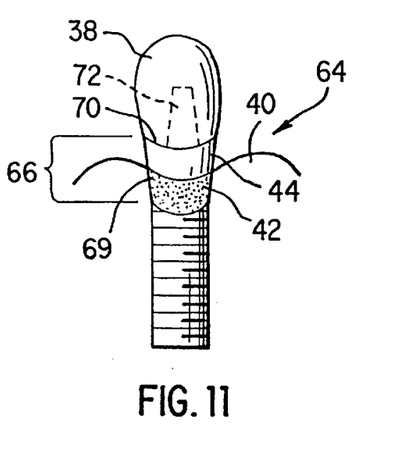
FIG. 11 depicts a frontal view of an implant according to another embodiment of the present invention.
Figure 12:
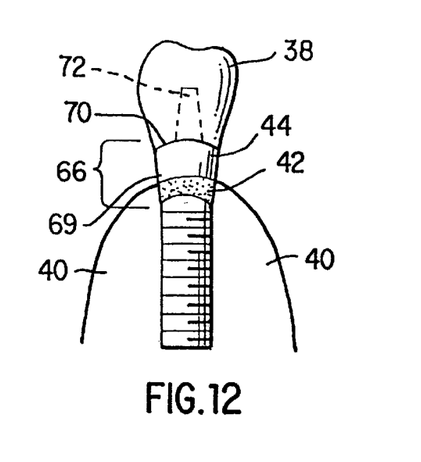
FIG. 12 depicts an interproximal view of the implant in FIG. 11.

A skilled artisan will readily recognize that the principles of the present invention can be equally applied to one-stage as well as two-stage processes. For example, FIGS. 9 and 10 show one-stage implant 58, according to another embodiment of the present invention. Implant 58 includes shaft 60, distal end 62, proximal end 64 and bonetissue/soft-tissue transition region 66 with scalloped bone-tissue apposition surface 42 and scalloped soft-tissue apposition surface 44, as substantially described above. Abutment 69 is permanently attached to the one-stage implant 58 as is well know in the art.

One-or two-stage implants, according to alternative embodiments of the present invention, may include either a planar abutment-crown interface 68 (FIGS. 3, 4, 9 and 10) or a contoured abutment-crown interface 70 (FIGS. 6, 7, 11 and 12), the latter of which substantially matches the natural contour of the alveolar bone. Contoured abutment-crown interface 70 allows for crown 38, in both one-and two-stage implants, to extend further towards the gum line, thereby resulting in a more aesthetically pleasing restoration. Chimney 72, or other means well known to the skilled artisan, is provided in both one-and two-stage implants according to the present invention for attaching crown 38 to the abutment.

Although various embodiments of the present invention have been described, the descriptions are intended to be merely illustrative. Thus, it will be apparent to the skilled artisan that modifications may be made to the embodiments as described herein without departing from the scope of the claims set forth below.

What is claimed is:

1. An endosseous dental implant, comprising:
   a shaft made from a biocompatible material, said shaft having a distal end and a proximal end;
   an abutment-implant interface disposed towards the proximal end of said shaft; and
   a bone-tissue apposition surface formed on said shaft and disposed adjacent to said abutment-implant interface, said bone-tissue apposition surface including a set of peaks and troughs configured to approximate the physiological contours of naturally occurring bone-tissue morphology.

2. The endosseous dental implant according to claim 1, wherein said bone-tissue apposition surface has a scalloped appearance.

3. The endosseous dental implant according to claim 2, wherein the highest points of said bone-tissue apposition surface substantially aligns with the interproximal areas of the bone-tissue, and wherein the lowest points of said bone-tissue apposition surface substantially aligns with the buccal and lingual area of the bone-tissue.

4. The endosseous dental implant according to claim 1 further comprising:
   a soft-tissue apposition surface formed on said shaft and disposed between said bone-tissue apposition surface and said abutment-implant interface, said soft-tissue apposition surface including a set of peaks and troughs configured to approximate the physiological contours of naturally occurring soft-tissue morphology.

5. The endosseous dental implant according to claim 1 further comprising:
   a means for connecting an abutment to said abutment-implant interface for use in a two-stage procedure.

6. The endosseous dental implant according to claim 5, wherein said abutment-implant interface has a substantially planar upper surface approximately 90° to the longitudinal axis of said shaft, and wherein said planar upper surface substantially surrounds said means for connecting.

7. The endosseous dental implant according to claim 5, wherein said abutment-implant interface has a contoured upper surface, and wherein said contoured upper surface substantially surrounds said means for connecting.

8. The endosseous dental implant according to claim 7, further comprising an abutment wherein a lower surface of the abutment substantially abuts against said contoured upper surface, thereby providing improved lateral support.

9. The endosseous dental implant according to claim 1, further comprising:
   an abutment permanently attached to said abutment-implant interface for use in a one-stage procedure.

10. The endosseous dental implant according to claim 9, wherein said shaft and said abutment are constructed from a single piece of material.

11. The endosseous dental implant according to claim 9, wherein said abutment has a substantially planar upper surface approximately 90° to the longitudinal axis of said shaft and wherein said planar upper surface substantially surrounds a chimney.

12. The endosseous dental implant according to claim 9, wherein said abutment has a contoured upper surface and wherein said contoured upper surface substantially surrounds a chimney.

13. A one-stage endosseous dental implant, comprising:
    a shaft made from a biocompatible material, said shaft having a distal end and a proximal end;
    a bone-tissue apposition surface formed on said shaft and disposed adjacent to said abutment-implant interface, said bone-tissue apposition surface including a set of peaks and troughs configured to approximate the physiological contours of naturally occurring bone-tissue morphology; and
    an abutment permanently attached to the proximal end of said shaft.

14. The one-stage endosseous dental implant according to claim 13, wherein said abutment has a substantially planar upper surface approximately 90° to the longitudinal axis of said shaft, and wherein said planar upper surface substantially surrounds a chimney.

15. The one-stage endosseous dental implant according to claim 13, wherein said abutment has a contoured upper surface and wherein said contoured upper surface substantially surrounds a chimney.

16. A two-stage endosseous dental implant system, comprising:
- a shaft made from a biocompatible material, said shaft having a distal end and a proximal end;
- a bone-tissue apposition surface formed on said shaft and disposed adjacent to said abutment-implant interface, said bone-tissue apposition surface including a set of peaks and troughs configured to approximate the physiological contours of naturally occurring bone-tissue morphology;
- an abutment-implant interface disposed at the proximal end of said shaft;
- an abutment configured to attach to said abutment-implant interface;
- a means for connecting said abutment to said abutment-implant interface; and
- a crown having a distal end configured to fit over said abutment.

17. The two-stage endosseous dental implant system according to claim 16, wherein said abutment-implant interface has a substantially planar upper surface substantially surrounding said means for connecting, and wherein said upper planar surface is approximately 90° to the longitudinal axis of said shaft.

18. The two-stage endosseous dental implant system according to claim 17, wherein said abutment has a substantially planar upper abutment-crown interface surface.

19. The two-stage endosseous dental implant system according to claim 17, wherein said abutment has a contoured upper abutment-crown interface surface substantially surrounding a chimney, and wherein a distal end of said crown is configured such that at least an outside surface of said crown extends to and follows the contours of said upper abutment-crown interface surface, thereby providing a narrow depth between the distal end of said crown and said bone tissue apposition surface.

20. The two-stage endosseous dental implant system according to claim 19, wherein said abutment-implant interface has a contoured upper surface substantially surrounding said means for connecting, and said contoured upper surface approximately matches the contour of the natural bone morphology, and wherein said abutment has a lower surface configured to substantially abut said contoured upper surface.

21. The two-stage endosseous dental implant system according to claim 20, wherein said abutment has a substantially planar upper abutment-crown interface surface.

22. The two-stage endosseous dental implant system according to claim 20, wherein said abutment has a contoured upper abutment-crown interface surface substantially surrounding a chimney, and wherein a distal end of said crown is configured such that at least an outside surface of said crown extends to and follows the contours of said upper abutment-crown interface surface, thereby providing a narrow depth between the distal end of said crown and said bone-tissue apposition surface.

23. A one-stage endosseous dental implant system, comprising:
- a shaft made from a biocompatible material, said shaft having a distal end and a proximal end;
- a bone-tissue apposition surface formed on said shaft and disposed adjacent to said abutment-implant interface, said bone-tissue apposition surface including a set of peaks and troughs configured to approximate the physiological contours of naturally occurring bone-tissue morphology;
- an abutment permanently attached to the proximal end of said shaft; and
- a crown having a distal end configured to secure to said abutment.

24. The one-stage endosseous dental implant system according to claim 23, wherein said abutment has a substantially planar upper surface substantially surrounding a chimney, and wherein said upper planar surface is approximately 90° to the longitudinal axis of said shaft.

25. The one-stage endosseous dental implant system according to claim 23, wherein said abutment has a contoured upper surface substantially surrounding a chimney, and wherein said contoured upper surface approximately matches the contour of naturally occurring bone-tissue morphology.

26. The one-stage endosseous dental implant system according to claim 25, wherein a distal end of said crown is configured such that at least an outside surface of said crown extends to and follows the contours of said contoured upper surface, thereby providing a narrow depth between the distal end of said crown and the bone-tissue apposition surface.

* * * * *